Aug. 27, 1974 A. BARBERET ET AL Plant Pat. 3,602
CARNATION PLANT
Filed March 30, 1973
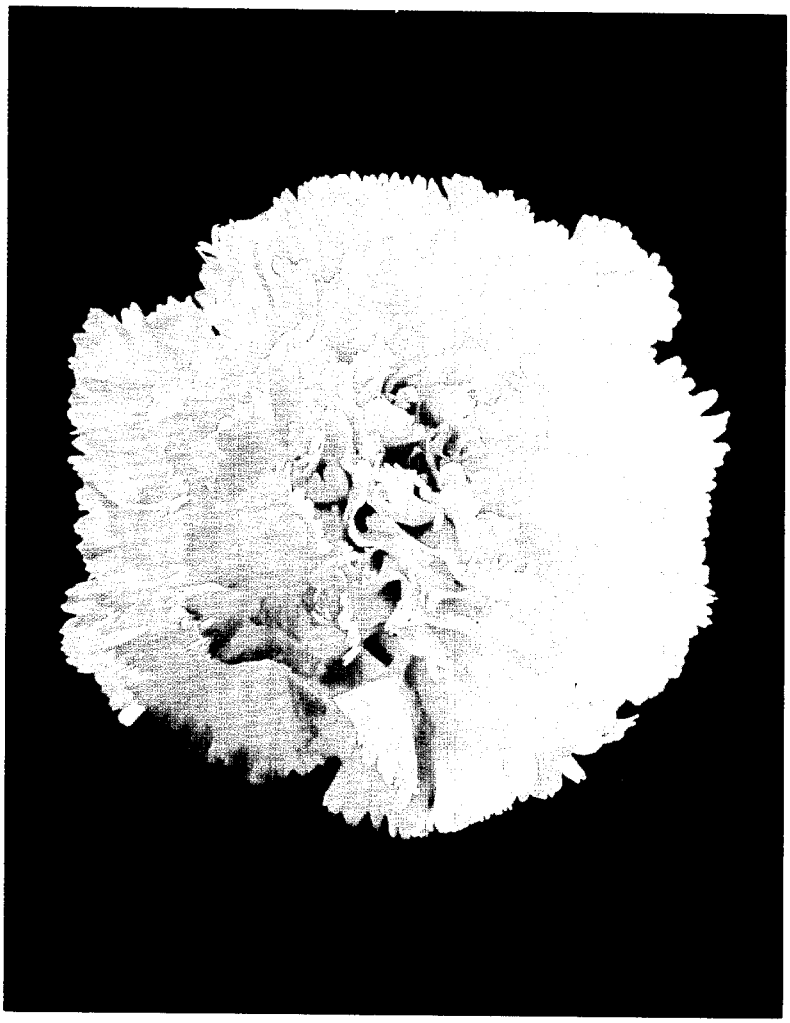

United States Patent Office

Plant Pat. 3,602

Patented Aug. 27, 1974

3,602

CARNATION PLANT

Alexandre Barberet and Henri Blanc, La Londa, France, assignors to Laboratoire de Physiologie Vegetale de La Londe Barberet & Blanc, La Londe, France Filed Mar. 30, 1973, Ser. No. 346,717
Claims priority, application Italy, Dec. 22, 1972, 33,459/72
Int. Cl. A01h 5/00
U.S. Cl. Plt.—72 1 Claim

ABSTRACT OF THE DISCLOSURE

A new variety of carnation plant suitable for greenhouse culture for the production of cut flowers, particularly distinguished by the more homogeneous size of its relatively large flowers, its very long floral stems, and the deeper pink coloring of its blooms.

BACKGROUND OF THE NEW PLANT

Our new variety of carnation plant was discovered by us in 1970 as a sport or mutation of the variety "Flamingo" (unpatented) growing under glass in our laboratories at La Londe, France. The deep pink coloring of this sport and its unusually long floral stems resulted in its being selected for reproduction; and asexual propagation of this sport by cuttings and under our direction, at La Londe, France, has demonstrated that its distinctive characteristics of blossom size, stem length, and coloring are fixed and hold true from generation to generation.

DESCRIPTION OF THE DRAWING

This new variety of carnation plant is illustrated by the accompanying photographically produced, full color drawing which shows a face view of the fully opened blossom, the color shown being as nearly true as it is reasonably possible to obtain by conventional photographic procedures.

DESCRIPTION OF THE NEW PLANT

The following is a detailed description of our new variety of carnation plant based upon observations made on Nov. 8, 1972, of greenhouse plants set out in April 1971, the color characteristics being identified according to the R.H.S. Colour Chart issued by The Royal Horticultural Society, at London, England.

THE PLANT

Origin: Sport.

Parentage: The unpatented variety "Flamingo" belonging to the family of American carnations derived by mutation of the cultivar "William Sim" (Plant Pat. 669).

Classification:

*Botanic.*—*Dianthus caryophyllus* L.

*Commercial.*—Perpetual flowering carnation.

Form: Bush, of the Sim type.

Height: Foliage to height of about 50 cm. At 18 months, the plant flowers at an average height of about 115 cm. on principal stems extending about 107 cm. from attachment to main stem.

Growth: Vigorous and erect, principal stems having an average diameter of 0.8 cm.

Branching: Normal, with 4 to 6 strong, upright flowering branches.

Foliage: Quantity—not abundant and occurring mainly at the lower part of the plant.

*Size of Leaf.*—Large, up to about 12.9 cm. long and about 126 cm. wide.

*Form of Leaf.*—Lanceolate with acuminate apex and entire margins. Leaves extend upward from the stem and then hang downward or become downwardly curled.

*Texture.*—Smooth.

*Color.*—Leaves—Greyed Green 189B. Stems, between joints—Lower third of stem—Green 138C to 139D; upper part of stem—Greyed Green 189B to 189C., Joints of stem—Greyed Green 193C.

*Ribs.*—Single prominent central rib. Leaves at the middle of the stem length also distinguished by the additional parallel ribs showing on the under side.

*Petioles.*—None, leaf is decurrent and amplexicaul.

THE BUD

Calyx:

*Form.*—Conical at beginning, then ovoid and finally cylindrical and wide-mouthed at opening of the sepals.

*Size.*—Medium. Diameter: About 22 mm. at mouth. Length: About 3 cm.

*Number per Stem.*—4 to 5.

*Opening.*—Slowly.

*Sepals.*—Curl back. Color: Inside—Pale Green; outside—Light Green. Shape: Ovate. Aspect: Smooth.

*Splitting.*—Calyx rarely splits.

Peduncles: Thick and relatively stiff.

THE FLOWER

Blooming Habit: Profuse and continuous.

Size of Bloom: Medium, averaging about 8.6 cm. in diameter and about 4.3 cm. in depth.

Borne: Singly on its stem, after cutting for sale as a cut flower.

Shape: High center, changing to dome-shaped as flower matures.

Petalage: Fully opened blossom—45 to 50 petals, averaging about 52, in more-or-less imbricated arrangement.

*Form.*—Fan shaped petals with rumpled or irregular body area and deeply serrated margins. Petals sometimes have whitish streaks.

*Color.*—Body of petal—Red Group 43C on both upper face and under face. Sometimes the streaks on the central petals have a pale rose color. Base of petal—Red Group 43D.

*Appearance.*—Satiny. Texture: Soft.

Petaloids: About 6 in number, half the size of the petals.

*Color.*—Red Group 43C.

Peduncle: Erect and almost rigid.

Persistence: Petals hang on and dry.

Fragrance: Just perceptible.

Disease Resistance: Very good for all current diseases as observed at La Londe, France.

Lasting Quality:

*On plant.*—15 days.

*As cut flower.*—10 to 12 days in stable ambient temperature of about 23° C.

REPRODUCTIVE ORGANS

Stamens:

*Anthers.*—None.

*Filaments.*—1 to 2 cm. long and of white color.

Pistils: 2 or 3 in number, 3.5 cm. long when tipped and of rose color.

Stigmas: Color—White and slightly reddish.

Ovaries: Cone shaped, whitish at base and greenish in middle part; yellowish at the top.

This new variety of carnation plant most nearly resembles the variety "Shocking" (unpatented) and while the coloring of its blossoms is in the color category of "Flamingo" and "Shocking," the shade of the color of this new variety is deeper and more intense. With respect to "Flamingo" and "Shocking," this new variety produces larger flowers of more homogeneous size and especially on very long floral stems. The new plant is also strong and vigorous in its growth habit and it provides a continuous production of attractive strong-stemmed flowers.

We claim:

1. A new and distinct variety of carnation plant, substantially as herein shown and described, characterized by the more intense coloring and homogeneous size of its flowers, and by its very long floral stems.

No references cited.

ROBERT E. BAGWILL, Primary Examiner